United States Patent [19]

Turco et al.

[11] Patent Number: 4,708,866

[45] Date of Patent: Nov. 24, 1987

[54] ARTIFICIAL NAIL COMPOSITION

[76] Inventors: Josephine M. Turco; Deborah A. Turco, both of 13 Bluebird La., West Amherst, N.Y. 14228

[21] Appl. No.: 764,122

[22] Filed: Aug. 9, 1985

[51] Int. Cl.⁴ .................. A61K 7/04; A61K 31/78
[52] U.S. Cl. ............................................. 424/61; 424/81
[58] Field of Search ................................. 424/61, 81

[56] References Cited

U.S. PATENT DOCUMENTS 4,070,451  1/1978  Price ................................. 424/61
4,104,333  8/1978  Lee, Jr. et al. ................... 424/61

FOREIGN PATENT DOCUMENTS 2854556  6/1979  Fed. Rep. of Germany ........ 424/61

Primary Examiner—Alan Siegel
Attorney, Agent, or Firm—James J. Ralabate

[57] ABSTRACT

A self-curing nail composition containing methacrylate monomers, methacrylate polymers, calcium containing composition and a lubricant.

6 Claims, No Drawings

ARTIFICIAL NAIL COMPOSITION

This invention relates to a composition useful for the formation of artificial nails and, more particularly, to a self-curing coating that can be applied to human nails.

BACKGROUND OF THE INVENTION

It is known in the prior art to apply artificial nails to the surface of natural human fingernails. One method used is to attach an artificial preformed fingernail or portion of a fingernail to the natural nail by means of an adhesive. After these artificial nails are attached to the natural nail they must be filed at their lower terminal surface portion to blend with the natural nail. The result is, in many cases, not natural appearing since quite often the junction of the artificial nails tends to bend, become separated or become distorted when worn and must be removed or replaced. A typical artificial nail of this type is disclosed in U.S. Pat. No. 2,941,535. The adhesive disclosed in this prior art patent comprises a polymerizable acrylic ester monomer such as alkymethacrylate which has a filler formulated therewith. An additional drawback to this type nail is that the nail must be provided with holes to permit the adhesive to bond properly to the natural nail. Other preformed nails, molds, coatings or film formed nails are disclosed in U.S. Pat. Nos. 3,037,514; 3,157,912; 3,425,426 and 3,483,289.

Some prior art patents deal with mending broken fingernails and others with the use of substances applied to the nail surface to strengthen the natural nail. In most of these compositions, the hardenable substance is applied directly to the surface of nails and allowed to dry and harden. A large portion of these prior art compositions contain lower alkymethacrylate monomers and polymers. Usually these compositions are formulated from a powder mix and a compatible liquid. The liquid generally contains a polymerization accelerator and the powder a polymerization initiator. The powder when mixed is allowed to substantially dissolve in the liquid and when the methacrylate polymerizes the material cures and hardens. Many components are incorporated into these prior art compositions such as colorants, color stability agents and others. Typical coatings for nails are disclosed in U.S. Pat. Nos. 4,104,333; 4,229,431; 4,260,701 and 4,495,172.

In U.S. Pat. No. 4,104,333 a self-curing artificial nail composition is disclosed which contains a cross-linkable monomer such as ethylene glycol dimethacrylate, a furfuryl methacrylate, benzoyl peroxide, a tertiary amine-type accelerator, a polymeric filler and a flexibilizing material. The set time for the compositions of this prior art invention, usually about 120 to 400 seconds, may be regulated by varying the concentration of initiators and/or accelerators. Inorganic fillers such as finely divided alumina silicates, silica, quartz, glass and the like may be used to control consistency of material and improve its physical mechanical properties.

Generally, as suggested hereinbefore, a polymeric filler material which may be soluble, partially soluble, or insoluble in the resin matrix is present. Typically, but not necessarily, these polymers or copolymers of the monomeric materials are used in the in-situ polymerization composition. Suitable in prior art compositions and for the compositions of the present invention are copolymers of ethyl and methylmethacrylate, polyethylmethacrylate, polymethyl methacrylate, polymethyl acrylate, polyethyl acrylate and polypropyl acrylate. In other words, polymers of the monacrylates herein contemplated are suitable. The above-mentioned fillers are usually present in a concentration of less than about 40%, preferably from about 5% to about 55% by weight. Minor conventional amounts of modifiers may also be present such as dyes, opaquing agents (e.g. titanium dioxide), and stabilizers (e.g. 3-butyl-4-hydroxytoluene).

In U.S. Pat. No. 4,229,431 a method of forming a coating for a human nail is disclosed and claimed. In this prior art patent a flowable material containing methacrylate monomers and polymers is applied to the nail and allowed to harden in-situ on the nail. It is then formed to the desired shape by filing and the like. The composition used in this prior art patent is a two component powder-liquid formulation having the following typical make-up:

| | Percent by Weight |
|---|---|
| Part A (Powder) | |
| 70/30 copolymer of ethyl and methyl methacrylate | 99.1 |
| benzoyl peroxide (catalyst) | 0.8 |
| titanium dioxide (opaquing agent) | 0.1 |
| Part B (Liquid) | |
| methyl methacrylate | 78.35 |
| polyethylene glycol dimethacrylate | 20.0 |
| dimethyl-p-toluidine (accelerator) | 1.0 |
| 2-hydroxy-4-methoxy benzophenone (UV-absorber) | 0.5 |
| 3-butyl-4-hydroxy toluene (stabilizer) | 0.05 |
| dye | 0.1 |

In this patent, both parts (be they liquid/powder or paste/paste) are applied separately and mixed directly on the nail. Alternatively, both parts may be pre-mixed immediately before application on the nail or substrate elongator.

In U.S. Pat. No. 4,260,701 a fingernail coating composition having an acrylic binder, a peroxide catalyst, a tertiary amine accelerator and a polymeric filled soluble in the coating is disclosed. The acrylic binder contains a mono-ethylenically unsaturated monomer comprising at least a major proportion of methoxyethyl methacrylate.

In U.S. Pat. No. 4,495,172 a coating composition is disclosed. The coating composition comprises a curable ethoxyethylmethacrylate monomer, a polyethylmethacrylate homopolymer or copolymer filler and a cross-linking agent. The method involves applying the coating composition upon nails and curing the composition. The product involves a separately packaged liquid and powder, wherein the liquid comprises ethoxyethylmethacrylate monomer and a cross-linking agent and the powder comprises a polyethylmethacrylate and filler.

While the compositions disclosed in 4,495,172; 4,260,701; 4,229,431 and 4,104,333 are appropriate for forming curable artificial nail compositions, they also possess certain inherent drawbacks. In some instances the nail composition dries to a surface that does not have the appropriate color or texture of a natural nail. Some of these prior art compositions easily separate from the human nail when dried or worn. In other instances the broken or damaged nail being covered does not heal or grow strong while being covered by the artificial nail. In other instances a fungus or other infection occurs in the space between the natural and artificial nail. Also, prior art artificial nails have a tendency to crack easily and are required to be worn for long periods of time before the natural nail is repaired and healed.

SUMMARY OF THE INVENTION

It is therefore an object of this invention to provide an artificial nail composition devoid of the above-noted disadvantages.

Another object of this invention is to provide an artificial nail composition that appears more natural than the heretofore used materials.

Still a further object of this invention is to provide a human nail coating composition that bonds extremely well and will not easily separate from the natural nail.

A still further object of this invention is to provide a nail coating composition that nourishes and promotes the effective growing and repair of the coated natural nail.

Another still further object of this invention is to provide a nail coating that will not easily crack or become damaged or distorted when worn.

A yet still further object of this invention is to provide a nail coating composition that, because it encourages growth of the natural nail, need not be worn for the lengthy period of time required of prior art compositions.

The foregoing objects and others are accomplished in accordance with the present invention generally speaking by a novel improved nail coating composition. The composition herein disclosed comprises an acrylic binder, a peroxide catalyst, an alkylmethacrylate monomer, an akylmethacrylate polymer, a colorant, calcium carbonate and a lubricant such as lanolin. An improvement provided by this invention involves the use of a specified and controlled amount of a calcium containing composition such as calcium carbonate and a suitable lubricant. They may be used together with several compositions including the above-discussed prior art materials. The calcium-containing composition could only optimumly aid in the curing of the normal nail if the artificial nail is maintained intact and not substantially cracked or damaged. The lubricant such as lanolin provides this necessary artificial nail protection, that is, to prevent or minimize the chances of it cracking. Thus, the calcium composition and lubricant such as lanolin must both be present in effective amounts for proper functioning of this invention, one without the other would not provide the required beneficial curing of the natural nail.

As noted earlier, the present formulation involves the use of liquid and powder components. The liquid contains a lower alkylmethacrylate monomer such as methylmethacrylate. The powder contains a polymerized lower alkylmethacrylate such as polymethylmethacrylate. The liquid also contains a polymerization accelerator such as a tertiary amine and the powder a polymerization initiator such as peroxide which causes the composition to cure in-situ on the surface of the natural nail. Any suitable initiator such as lauroyl peroxide or benzoyl peroxide may be used. Any suitable initiator or accelerator such as tertiary aromatic amine and such as those disclosed in U.S. Pat. No. 4,495,172 may be used in the present invention.

In the specific nail coating compositions of the present invention, a chemically initiated curing technique is preferred. Thus, in order to induce curing of the nail coating compositions of the present invention, a free-radical catalyst may be incorporated into the coating components. Organic peroxide initiators such as lauroyl peroxide and especially benqoyl peroxide are preferred. The technique used to mix and polymerize the components of the present invention is as disclosed in the above-discussed prior art patents and in the *Encyclopedia of Polymer Science and Technology,* John Wiley and Sons, Inc., Vol. 1, pp. 263–97 (1964), all of which are incorporated by reference into this disclosure.

The ability of the initiator to cure the nail coating composition may be enhanced through the use of these activators or accelerators. Thus, a peroxide initiator can be activated with a tertiary aromatic amine such as an N,N-di (lower) alkyl-p-toluidine e.g., N,N-dimethyl-p-toluidine, N,N-diethyl-p-toluidine, and especially N,N-bis(2-hydroxyethyl-p-toluidine).

The various components of the nail coating composition may be combined in any suitable manner, and any of the compositions of the above-discussed prior art patents may be used together with the calcium composition and lubricant lanolin-containing materials of this invention. However, since chemically initiated polymerization starts immediately upon a mixture of all three of (1) methacrylic monomers, (2) an initiator and (3) an activator, it is necessary to separate at least one of these components from the others until immediately before the application of the nail coating to human nails. This separation may be achieved through the use of a two-package product, wherein various components of the nail coating composition are separately contained until the time of application to nails.

The polymerizable acrylic ester monomers used in the invention are selected from ethylmethacrylate, methylmethacrylate butyl methacrylate and mixtures thereof. These acrylic esters preferably have a polymeric filler dissolved therein.

The monomers used in the present invention are also either ethylmethacrylate, methylmethacrylate, butyl methacrylate and mixtures thereof.

In the preferred embodiments of this invention calcium or calcium carbonate and lanolin are added to a formulation comprising methylmethacrylate monomer, methylmethacrylate polymer or resin, acrylic ester polymer, benzoyl peroxide and colorants such as titanium dioxide or silica colorants. Other additives may be added to this formulation, for example, a mixture of methacrylic acid and isobutyl methacrylate when applied to the natural nail forms a good base for the artificial nail to be coated thereon. Also, it was found that using Fantasia (a registered Trademark of Fantasia Industries Corporation) on the natural nail before application or applied with the composition of this invention is preferred and provides many optimum results. These results include a smoother surface to the artificial nail and good adhesion of the artificial nail to the natural nail. It also avoids the necessity of filing the surface of the natural nail before applying the artificial nail composition of this invention. In addition, it assists in encouraging faster new nail growth and stronger new nail growth. The preferred composition containing Fantasia comprises protein, panthenol, aloe, allantoin, collagen, clotin, vitamins A,B,D and E, calcium, phosphorous, and natural botanicals in a gently acid base.

It has been found that while prior art formulations form artificial nails that are sometimes esthetically acceptable, they do little to promote the growth of the natural nail which is overcoated. In addition, prior art nails crack easily and upon drying too often separate from the natural fingernail. To correct these deficiencies, calcium or calcium carbonate and a lubricant such as lanolin are added to the formulation. The calcium carbonate assists in not only healing of the coated natural nail but also allows the nail to grow strong and natural and enhances the subsequent color of the grown natural nail. It is important, however, for proper healing that the overcoating artificial nail not crack or separate. It is common for a natural nail to be distorted, soft and weak when the artificial nail is removed. When the present composition is used, a firm, faster growing and strong natural nail is substantially improved. Not only does the natural nail prosper, but the artificial nail formed by the present composition looks more natural and has more normal-like consistency than those compositions heretofore used. The lanolin in the present composition prevents or minimizes cracking of the artificial nail thus permits the calcium to function properly in healing the natural nail. Cracking is often caused by the nail composition drying too rapidly when applied to the natural nail. The lanolin prevents rapid drying and has the bonus effect of providing excellent adhesion of the composition to the natural nail. The rapid drying could cause cracks or uneven outer surface. Separating of the artificial nail from the natural nail is maintained to a minimum also by the use of lanolin in the present composition. Thus, the calcium carbonate in the present composition can strengthen the natural nail, stimulate growth of the natural nail and reduces the time needed to wear the artificial nail. The lanolin prevents cracking of the artificial nail by reducing its brittleness, minimizes separation of the artificial nail from the natural nail and prevents too rapid drying of the composition. Since the lanolin maintains the integrity of the artificial nail the calcium can properly aid int he healing of the natural nail.

DESCRIPTION OF EXAMPLES AND PREFERRED EMBODIMENTS

The composition of the present invention will be more fully described by reference to the following examples. Parts are by weight unless specified to be otherwise.

EXAMPLE I

A nail composition as formulated as follows:

| Ingredient | Percent |
| --- | --- |
| methyl methacrylate monomer | 30% |
| methyl methacrylate polymer | 30% |
| calcium carbonate | 15% |
| benzoyl peroxide | 2% |
| lanolin | 15% |
| acrylic ester polymer | 6% |
| titanium dioxide (opaquing agent) | 2% |
| (silica colorant added as needed to color and appropriate polymer acceleration added) | |

EXAMPLE II

| Ingredient | Parts by Weight |
| --- | --- |
| copolymer of ethyl and methyl methacrylate | 50 |
| methyl methacrylate polymer | 50 |
| calcium carbonate | 12 |
| titanium dioxide | 3 |
| lanolin | 12 |
| benzoyl peroxide | 1 |
| methyl methacrylate monomer | 60 |
| mixture of methacrylic acid and isobutyl methacrylate | 20 |

EXAMPLE III

| Liquid | % Weight | Powder | % Weight |
| --- | --- | --- | --- |
| Ethoxyethyl methacrylate | 95 | Copolymer of polyethyl and polymethyl-methacrylate | 98.9 |
| Diethyleneglycol dimethacrylate | 2 | | |
| N,N—bis (2-hydroxyethyl)-p-toluidine | 2.9 | Benzoyl peroxide | 1 |
| BHT (inhibitor) | 0.1 | Titanium dioxide | 0.1 |

The above material was mixed at a 1.2 ratio of liquid to powder and 10% calcium carbonate and 10% lanolin was added. It cured forming a flexible and non-brittle polymer.

EXAMPLE IV

| Ingredient | Parts by Weight |
| --- | --- |
| methyl methacrylate monomer | 50 |
| polymethyl methacrylate | 50 |
| benzoyl peroxide | 1.0 |
| titanium dioxide | 0.2 |
| triethylene glycol dimethacrylate | 25.0 |
| cyclohexyl methacrylate | 15.0 |
| calcium carbonate | 7.0 |
| lanolin | 7.0 |
| mixture of methacrylic acid and isobutyl methacrylate | 5.0 |

EXAMPLE V

| Ingredient | Parts by Weight |
| --- | --- |
| methyl methacrylate monomer | 50 |
| methyl methacrylate polymer | 25 |
| ethyl methacrylate polymer | 25 |
| calcium carbonate | 20 |
| lanolin | 10 |
| titanium dioxide | 2 |
| benzoyl peroxide | 0.8 |
| silica colorant | 0.5 |
| acrylic ester polymer | 7 |

The amount of lanolin was varied in each of the above examples from 2-50 parts in each composition. In addition, the compositions of each of the above examples were used or mixed with Fantasia both before and during application to the nail.

The above materials in Examples I-V were mixed as follows:

The methacrylate polymer is in powder form combined with benzoyl peroxide and titanium dioxide. This powder is mixed in a blender with the methacrylate monomer, lanolin and calcium. It is mixed for about 5 minutes until a cloudy solution results. It is then ready for use or storage. The calcium may be in the form of calcium carbonate or calcium crystals, powder or other solid form. The resulting composition mix may be applied to the human nail by a brush or other applicator.

The lanolin in the composition of this invention has the bonus effect of preventing the brush from hardening after one use.

Other ingredients may be added to the formula of this invention to enhance or otherwise add to the beneficial effects of the formula. The preferred and optimumly preferred embodiments of the present invention have been described herein to illustrate the underlying principles of the invention, but it is to be understood that numerous modifications and ramifications may be made without departing from the spirit and scope of this invention.

What is claimed is:

1. An artificial nail composition for coating human nails comprising in combination from 5-50 parts of a lower alkylmethacrylate monomer, from about 5-50 parts of a lower alkylmethacrylate polymer, from about 0.1 to 5.0 parts of a polymerization initiator, from about 0.1 to 5.0 parts of a polymerization accelerator, from about 2.0 to 30 parts of a calcium composition, and from about 2.0 to 50 parts of lanolin, said lower alkylmethacrylates selected from the group consisting of methyl, ethyl, butyl methacrylates and mixtures thereof, said calcium composition selected from the group consisting of calcium, calcium carbonate and mixtures thereof.

2. The composition of claim 1 wherein said polymer is polymethylmethacrylate.

3. The composition of claim 1 wherein said initiator is benzoyl peroxide.

4. The compositoion of claim 1 wherein said accelerator is a tertiary aromatic amine.

5. The composition of claim 1 wherein said polymer is a copolymer of ethyl and methylmethacrylate.

6. The composition of claim 1 wherein said composition comprises "FANTASIA".

* * * * *